United States Patent
Hwang et al.

(10) Patent No.: US 11,577,064 B2
(45) Date of Patent: Feb. 14, 2023

(54) METHOD AND DEVICE FOR MANUFACTURING MICRONEEDLE HAVING COATING PART ON TIP THEREOF

(71) Applicant: LG HOUSEHOLD & HEALTH CARE LTD., Seoul (KR)

(72) Inventors: Young-Min Hwang, Daejeon (KR); Woo-Sun Shim, Daejeon (KR); Nae-Gyu Kang, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 251 days.

(21) Appl. No.: 16/766,544

(22) PCT Filed: Jul. 5, 2018

(86) PCT No.: PCT/KR2018/007658
§ 371 (c)(1),
(2) Date: May 22, 2020

(87) PCT Pub. No.: WO2019/103268
PCT Pub. Date: May 31, 2019

(65) Prior Publication Data
US 2020/0324096 A1    Oct. 15, 2020

(30) Foreign Application Priority Data
Nov. 24, 2017   (KR) .................. 10-2017-0158495

(51) Int. Cl.
*A61M 37/00*       (2006.01)
*B29C 33/38*       (2006.01)
(Continued)

(52) U.S. Cl.
CPC ..... *A61M 37/0015* (2013.01); *B29C 33/3857* (2013.01); *B29C 41/22* (2013.01);
(Continued)

(58) Field of Classification Search
CPC ...... A61M 37/0015; A61M 2037/0023; A61M 2037/0053; A61M 2037/0046;
(Continued)

(56) References Cited

U.S. PATENT DOCUMENTS

2002/0133129 A1*  9/2002  Arias ............... A61B 5/150419
                                          264/225
2008/0213461 A1*  9/2008  Gill ...................... A61K 9/0021
                                          427/2.3
(Continued)

FOREIGN PATENT DOCUMENTS

CN       101935011 A      1/2011
CN       102395354 A      3/2012
(Continued)

OTHER PUBLICATIONS internetionei Search Report (PC17ISA210) issued in PCT/KR2018/007658 dated Nov. 13, 2018.

*Primary Examiner* — Amber R Stiles
(74) *Attorney, Agent, or Firm* — Birch, Stewart, Kolasch & Birch, LLP

(57) ABSTRACT

The present disclosure relates to a method for manufacturing a microneedle containing a coating part on a needle tip and an apparatus used for the method. When a microneedle is manufactured using the coating method and apparatus according to the present disclosure, a coating part in which a target material is impregnated can be easily inserted into skin and effective dissolution is possible. Further, the target material is allowed to show excellent skin permeability with the dissolution of the coating part of the microneedle manufactured according to the present disclosure, thereby a quantitative amount of target material can be effectively delivered into the skin.

8 Claims, 2 Drawing Sheets

(51) Int. Cl.
  *B29C 41/22* (2006.01)
  *B29C 41/38* (2006.01)
(52) U.S. Cl.
  CPC ..... *B29C 41/38* (2013.01); *A61M 2037/0023* (2013.01); *A61M 2037/0053* (2013.01)
(58) Field of Classification Search
  CPC ..... B29C 33/3857; B29C 41/22; B29C 41/38; B29C 39/026; B29C 33/56; B29C 45/0053; B29C 2045/0079; B29C 45/263; B29C 33/48; B29C 41/02; B29C 2033/0094; B29K 2995/0062; B29K 2909/02; B29L 2031/7544
  See application file for complete search history.

(56) References Cited

U.S. PATENT DOCUMENTS

| | | | |
|---|---|---|---|
| 2008/0294116 A1 | 11/2008 | Wolter et al. | |
| 2009/0131887 A1 | 5/2009 | Shlomitsu et al. | |
| 2009/0234301 A1 | 9/2009 | Tomono | |
| 2011/0152792 A1 | 6/2011 | Takada | |
| 2011/0237925 A1 | 9/2011 | Yue et al. | |
| 2011/0276003 A1 | 11/2011 | Lïtge et al. | |
| 2013/0012882 A1 | 1/2013 | Quan et al. | |
| 2017/0050010 A1* | 2/2017 | Mcallister | B33Y 80/00 |
| 2017/0327963 A1* | 11/2017 | Chai | B29C 33/40 |

FOREIGN PATENT DOCUMENTS

| | | |
|---|---|---|
| CN | 104069585 A | 10/2014 |
| KR | 10-2007-0086221 A | 8/2007 |
| KR | 10-2013-0007615 A | 1/2013 |
| KR | 10-2015-005137 A | 1/2015 |
| WO | WO 2008/004597 A1 | 1/2008 |
| WO | WO 2008/062832 A1 | 5/2008 |

\* cited by examiner

[FIG. 1]
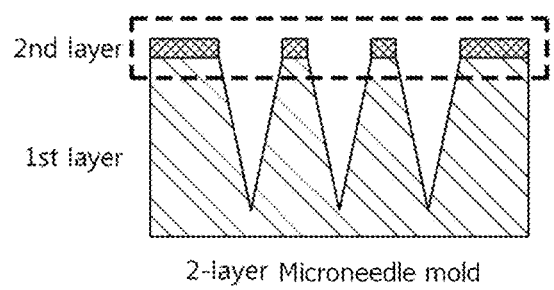
2-layer Microneedle mold
[FIG. 2]
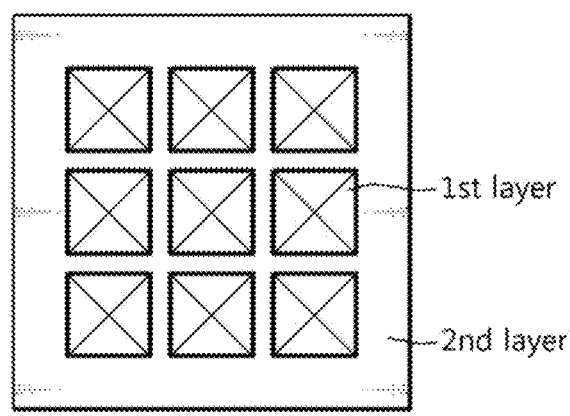

[FIG. 3]
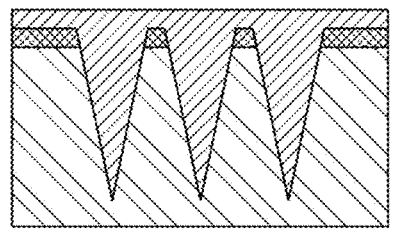
Microneedle manufacturing
[FIG. 4]
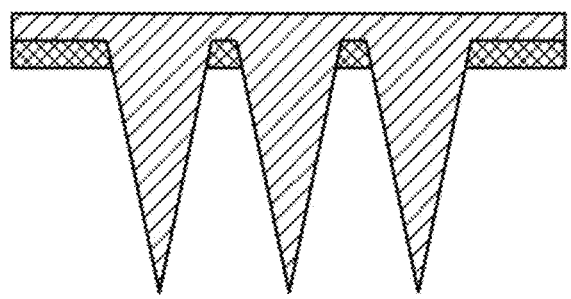
1st layer removing
[FIG. 5]
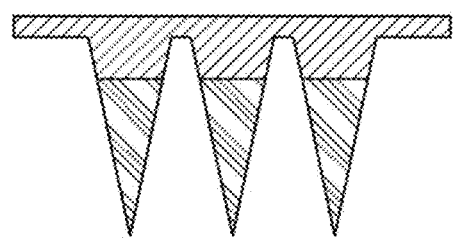

METHOD AND DEVICE FOR MANUFACTURING MICRONEEDLE HAVING COATING PART ON TIP THEREOF

DISCLOSURE

Technical Field

The present application claims the benefit of priority based on Korean Patent Application No. 10-2017-0158495 filed on Nov. 24, 2017, and the entire contents disclosed in the description and drawings of the corresponding application are incorporated in the present application.

The present disclosure relates to a method for manufacturing a microneedle containing a coating part on a needle tip and an apparatus used thereto. More specifically, the present disclosure relates to a method for manufacturing a microneedle so that the coating part in which a target material is impregnated is formed only on the needle tip and a microneedle mold which can be used for the method.

Background Art

Various methods for dermal administration of a target material with high efficiency have been studied. However, since the skin surface layer has a barrier function to prevent foreign substances from entering the body, it is very difficult not only to absorb the target material in an amount sufficient to exert the desired effect, but also to provide the target material to a specific site of the skin surface layer. Moreover, depending on characteristics of the target material, it is particularly difficult to supply a target material with very low bioavailability or pharmacological utilization rate through the skin, such as when skin affinity (lipid affinity) is insufficient or when the molecular weight is too large (500 Daltons or more).

Accordingly, in order to sufficiently supply the target material regardless of the type of the target material to a specific site of the skin surface layer, recently, a microneedle (micropile, micromissile capsule, etc.) technology has been proposed. In general, a microneedle is used for the delivery of an active substance such as a cosmetic active substance, a drug or a vaccine or the like in vivo, detection of an analyte in vivo and biopsy. As a material of the microneedle, a metal or silicone may be used, and may be made of a self-degradable material or a biodegradable material.

The microneedle is characterized by no pain and no bleeding even when inserted into skin, but it is very difficult to produce a microneedle that does not break or bend while retaining such a characteristic.

Nevertheless, as the fixation depth and the fixation time of the microneedle in skin are main factors directly affecting the skin permeability of the microneedle and the final skin supply of the target material, the need for development of a microneedle considering such factors continues to be raised.

DISCLOSURE

Technical Problem

Conventionally, when microneedles are pressed by hand and are inserted into skin, some microneedles are not inserted into skin and thus there is a problem that a target material hardly penetrates. In addition, a number of problems have been raised such that the target material comprised in the rear end of the microneedle is not supplied to skin but remains outside the skin and is virtually discarded as it is, if the material coated on the microneedle is not sufficiently dissolved.

Accordingly, the present inventors have researched and tried to provide a method for manufacturing a microneedle which can deliver a coating material effectively into skin as the coating material is present only on the tip which is to be inserted into skin, and an apparatus used thereto, and as a result, they have developed a method for manufacturing a microneedle of which tip is coated that not only solves all the aforementioned problems but also achieves high skin permeability and an apparatus used thereto, thereby completing the present disclosure.

Therefore, an object of the present disclosure is to provide a method for manufacturing a microneedle containing a coating part on a needle tip.

Another object of the present disclosure is to provide a microneedle mold which can be used for the manufacturing method.

Other object of the present disclosure is to provide a method for coating a microneedle using the microneedle mold.

Other objects and advantages of the present disclosure will become more apparent from the following detailed description of the invention, claims and drawings.

Technical Solution

One aspect of the present disclosure provides a method for manufacturing a microneedle containing a coating part on a needle tip, comprising (i) preparing a microneedle mold having a double-layered structure by attaching a masking film having hole(s) (second layer) on top of a mold structure having microneedle-shaped fine engraved patterns (first layer); (ii) injecting a needle-forming polymer composition into the mold having the double-layered structure; (iii) curing the injected composition to form a microneedle structure; (iv) removing the first layer to expose a needle tip of the formed structure; (v) coating the exposed needle tip with a coating solution; and (vi) removing the second layer.

Herein, skin is the surface of the body in contact with the outside world, and the skin includes cornea, oral soft tissue, gum, nasal mucosa and the like.

Herein, application to skin means adhering, pasting, preferably, inserting on the skin surface for dermal administration.

The microneedle according to the present disclosure is divided into a front end and a rear end, according to the direction of application (insertion) into skin, where the part which first contacts with skin when the microneedle is applied (inserted) into skin and includes a skin insertion end is called the front end, and the other part is called the rear end, and the rear end comprises a pressurizing end to which pressure is applied.

Herein, 'tip' means a skin insertion end, which is a protruding part comprising the end of the front end first contacting to skin when applying a microneedle into skin, and 'coating part' means a part in which a coating material is coated or attached on the microneedle surface.

Conventionally, as a masking method for coating a microneedle, a method of using fluid as a masking material and then removing it by evaporation was used; or a method of covering a cured microneedle with a masking film, coating the needle tip, and then removing the masking film layer was used.

These conventional methods need a process like evaporation, or has disadvantages in that the masking film's holes and the microneedle tips are easily misaligned from each other, and the defect rate is very high because the needle tips are damaged in the process of covering the microneedle cured in advance with the masking film layer.

Accordingly, the present inventors have developed a process of producing a microneedle mold having a double-layered structure at first by combining a masking film (second layer) to the conventional mold (first layer) in advance (FIG. 1), and then injecting a needle-forming polymer to the microneedle mold having the double-layered structure and curing it to manufacture a needle, and then removing the first layer and performing needle tip coating, and then removing the masking film (second layer), and thereby the present inventors can provide a method for manufacturing a microneedle with a significantly reduced defect rate.

It is not easy to accurately align the arrangement with the tips and there is a possibility of sharp tip damages, if the masking film is covered after the needle is formed as the microneedle is in a microstructure; but on the other hand, if the method of the present disclosure is used, the needle is manufactured and the coating is carried out in the state where the masking layer is first formed, and the masking layer is removed later, and therefore misalignment does not occur, so it is possible to coat the needle tips more precisely, and also has a very efficient advantage in terms of quantity and time.

In the method of the present disclosure, the mold structure having a microneedle-shaped fine engraved patterns (first layer) is composed of a single layer, and it may be a conventionally manufactured microneedle mold.

This microneedle mold structure or template may be commercially purchased from sellers such as Micropoint technology (https://micropoint-tech.com), Blueacretechnology, and the like, which sell various kinds of molds, for example, metal engraved molds, ceramic engraved molds or resin engraved molds, and the like and used.

In addition, it is possible to produce the microneedle mold structure (first layer), using a method for engraving a metal plate, a ceramic plate or a resin substrate by lithography method, or forming a microneedle mold structure by soft lithography and photo lithography methods using a photoresist material such as PDMS, etc., and the like.

When the microneedle mold structure is a resin engraved mold, the resin may be one or more selected from the group consisting of thermoplastic resins; acrylic resins, ABC-based resins, Nylon-based resins, PLA (Polylactic acid)-based resins, polybenzimidazole-based resins, polycarbonate-based resins, polyether sulfone-based resins, polyoxymethylene, PEEK (Polyether ether ketone)-based resins, polyethylene-based resins, polyphenylene oxide-based resins, polyphenylene sulfide-based resins, polypropylene-based resins, polystyrene-based resins, polyvinyl chloride-based resins, Teflon-based resins, polyester-based resins, polyurethane-based resins, polyurea/polyurethane hybrid resins, vulcanized rubber, phenol-formaldehyde, urea-formaldehyde, melamine resins, DAP (Diallyl-phthalate)-based resins, epoxy resins, epoxy novolac resins, phenolic resins, benzoxazine-based resins, polyimide-based resins, bismaleimide resins, polycyanurate, furan resins, silicone resins and vinyl ester-based resins, but not limited thereto.

The masking film in which holes are formed on top (second layer) used for the method of the present disclosure comprises one or more selected from the group consisting of silicone, polyurethane, polyethylene, polyester, polypropylene and poly vinyl chloride, but are not necessarily limited thereto.

The masking film is preferably a polymer film comprising a thermoplastic resin component, and it may be easily attached on top of the mold structure (first layer) by applying a little heat energy, or may be attached using an adhesive material, for example, an acrylic binder, a rubber-based binder, a hydrocolloid adhesive, and the like.

It is also possible to arrange the hole region so that no separation occurs in the hole region, by a method for stabbing the hole region of the double-layered structure mold using a microneedle, before injecting a needle-forming polymer composition after attaching the masking film on the mold structure.

Moreover, in the method of the present disclosure, the needle-forming polymer composition may comprise general synthetic and natural polymers, preferably, water-soluble polymers, or it may be composed by comprising an autolytic or biodegradable material.

According to one embodiment of the present disclosure, the needle-forming polymer composition may comprise one or more selected from the group consisting of hyaluronic acid; biodegradable polymers including poly(lactide), poly (glycolide), poly(lactide-co-glycolide), polyanhydride, polyorthoester, polyetherester, polycaprolactone, polyesteramide, poly(butyric acid), poly(valeric acid), polyurethane and copolymers thereof; and non-biodegradable polymers including polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefins, polyethylene oxide and copolymers thereof.

On the other hand, as the coating material of the microneedle according to the present disclosure, general synthetic and natural polymers, preferably, water-soluble polymers may be used, or autolytic or biodegradable materials may be used.

Preferably, as a material which is dissolved and absorbed in the body when inserted into skin, for example, hyaluronic acid, sodium carboxymethyl cellulose, vinyl pyrrolidone-vinyl acetate copolymer, polyvinyl alcohol, polyvinyl pyrrolidone, saccharide or mixture thereof may be used. As the saccharide, xylose, sucrose, maltose, lactose, trehalose or mixture thereof may be used.

More preferably, it may comprise hyaluronic acid, sodium carboxymethyl cellulose and saccharide, and most preferably, sodium carboxymethyl cellulose of 1-60% by weight, hyaluronic acid of 1-60% by weight and saccharide of 3-60% by weight based on the total weight of the composition for manufacturing a microneedle may be comprised.

It is much more preferable that the saccharide is trehalose. In this composition, the physical properties and highest synergistic effect of the microneedle corresponding to the diameter and aspect ratio range of the tip according to the present disclosure may be exhibited.

The coating material of the microneedle according to the present disclosure may further comprise a solubilizer, a plasticizer, a surfactant, a preservative, an anti-inflammatory agent, and the like. As the plasticizer, for example, polyols such as ethylene glycol, propylene glycol, dipropylene glycol, butylene glycol, glycerin, etc. may be used alone or in combination. In particular, as the result of several evaluations, glycerin is more preferable. As the solubilizer, various components known in the art may be appropriately selected and used. Preferably, as the result of various evaluations in aspect of physical properties and durability of the microneedle coating part, and compatibility with other materials forming the microneedle coating part, HCO-40 may be used.

The coating material of the microneedle may further comprise additional components (active ingredients) to cause an additive or synergistic effect depending on the target material.

The active ingredient may be an ingredient for drugs, vaccines, nutrients or cosmetics, depending on the use, but not limited thereto, and may include cells, proteins, nucleic acids, peptides, polysaccharides, lipids, Botox, vitamin C or its derivative, niacinamide, retinol or retinol derivative, arbutin, adenosine, kojic acid, caffeine, Selina, diosmetin, macelignan, Asiaticoside, polydatin, ginsenoside, prangenidin, hydroxy proline, and the like.

The active ingredient may be present for example, between materials forming the coating part of the microneedle (base compounds) in the form impregnated in the material coated on the microneedle tip, and it may be present in a form in which materials forming the coating part of the microneedle (base compounds) surround the target material, but not limited thereto.

According to a preferable embodiment of the present disclosure, the tip of the microneedle is inserted into skin and the coating material is dissolved, and therefore when the target material is contained in the coating part of the microneedle, there is no problem in administering it into skin and the target material can be substantially penetrated into the skin.

As above, the process for forming the coating part on the tip region of the microneedle may be performed for example, by a dipping or spraying method, but not limited thereto.

In addition, the present disclosure provides a method for manufacturing a microneedle patch containing a coating part in which a target material is impregnated on a tip of a microneedle, by further comprising adhering a support containing an adhesive to the formed microneedle structure, before removing the mold (first layer) after curing the needle-forming polymer composition.

Such a microneedle patch is also called a microneedle device or microneedle sheet.

Such a microneedle patch can insert the microneedle tip into skin by retaining one or more of microneedles on one side of the support and pressurizing the other side, and the coating part coated on the inserted needle tip region may be dissolved.

In this way, when a support comprising an adhesive is additionally adhered to the microneedle structure, the microneedle manufactured using the support may be easily separated from the mold (first layer).

The support comprising an adhesive may have adhesion on the side contacting to skin, and herein “adhesion” means a sticky property, and the degree of sticking is not particularly limited, and it is understood to have adhesion if the patch does not fall when it contacts to a certain contact surface such as skin, and the like.

The adhesive support (patch) is a skin adhesive patch, and a flexible material may be used in consideration of curves of skin, etc., and for example, an acrylic or rubber-based adhesive having adhesion may be applied to a sheet with a material such as polyurethane, polyethylene, polyester, polypropylene, polyvinyl chloride, and the like. The adhesive may be applied for example, in a thickness of 1 to 100 μm.

In one example, for the patch, a hydrocolloid adhesive may be used. The hydrocolloid adhesive may be in a form in which hydrophilic hydrocolloid particles are distributed to a hydrophobic polymer matrix by mixing a tackifier to a hydrophilic polymer and a hydrophobic polymer. The tackifier may include for example, rosin ester, and the like, and all the tackifier generally used for the hydrocolloid adhesive in the art may be included.

In another example, the hydrocolloid adhesive may be attached to the microneedle in a form laminated to a film of polyurethane, polyethylene, polypropylene, polyvinyl chloride or polyester material.

The form of the adhesive support is not particularly limited, and the form may be produced in consideration of contact possibility with skin, shapes of the microneedle array, and the like.

The adhesive support may comprise a number of micro-sized holes, and may have a structure in which moisture (or liquid) may be delivered to the microneedle along the holes. The number of holes is not limited, and it may be appropriately selected in consideration of difference in solubility depending on the material of the microneedle.

Furthermore, the adhesive support may comprise a drug or cosmetic component-containing matrix or reservoir. As above, when the skin adhesive support or patch contains a medical, pharmaceutical or cosmetic active ingredient, there is an advantage in that the active ingredient can rapidly move into skin from the patch.

The active ingredient comprised in the patch may be same or different from the active ingredient comprised in the aforementioned coating part.

The skin adhesive support may be composed of the same material as the aforementioned coating part of the microneedle, or a material with adhesive affinity may be used in addition to it. As the material with adhesive affinity, for example, an acrylic or rubber-based adhesive such as polyurethane, polyethylene, polyester, polypropylene, polyvinyl chloride, etc. is applied, or a hydrocolloid in which hydrophilic hydrocolloid particles are distributed to a hydrophobic polymer matrix by mixing a tackifier to a hydrophilic polymer and a hydrophobic polymer, and the like may be included, but not limited thereto.

Other aspect of the present disclosure provides a microneedle mold containing a coating part on a needle tip, characterized by having a double-layered structure in which a masking film (second layer) in which a hole is formed on top of a mold structure (first layer) having a microneedle-shaped fine engraved pattern, and a method for coating a microneedle using the same.

When a microneedle is manufactured using the double-layered structure mold and coating method, a masking layer may be used to form a coating layer only on the needle tip region, while significantly reducing the defect rate of the needle tip, and also, there is an advantage that the microneedle tip can be coated more efficiently in terms of quantity and time.

Advantageous Effects

When a microneedle is manufactured using the coating method and apparatus according to the present disclosure, a coating part in which a target material is impregnated can be easily inserted into skin and effective dissolution is possible. Further, the target material is allowed to show excellent skin permeability with the dissolution of the coating part of the microneedle manufactured according to the present disclosure, thereby a quantitative amount of target material can be effectively delivered into the skin.

BRIEF DESCRIPTION OF THE DRAWINGS

FIG. 1 is a schematic cross-sectional view of a microneedle mold manufactured by attaching a masking film having holes (second layer) onto a mold structure having fine engraved patterns (first layer).

FIG. 2 is a schematic plane view of a microneedle mold of a double structure in which a masking film is attached and formed.

FIG. 3 shows a state in which a needle-forming polymer composition is cured by injecting it into a microneedle mold of a double-layered structure.

FIG. 4 is a schematic view of a state in which a mold structure (first layer) is removed to expose the needle tips.

FIG. 5 is a schematic cross-sectional diagram of a manufactured microneedle having coated needle tips, by removing a masking film (second layer) after coating the needle tips;

MODE FOR INVENTION

Hereinafter, the present disclosure will be described in more detail by examples. These examples are intended to more specifically illustrate the present disclosure only, and it will be obvious that the scope of the present disclosure is not limited by these examples to those skilled in the art.

EXAMPLE

Step 1. Preparation of a Microneedle Coating Solution

As Table 1 below, a microneedle coating solution was prepared. Herein, the contents of the compositions are expressed in % by weight unless otherwise specified. After dissolving CMC (Carboxymethyl cellulose) in purified water, Tween 80 and Trypan blue were added to prepare the solution.

TABLE 1

| | Content (% by weight) |
|---|---|
| CMC | 8 |
| Tween 80 | 5 |
| Trypan blue | 15 |
| Water | to 100 |

Step 2. Manufacture of a Double-Layered Mold With an Attached Film for Masking

Areas of a microneedle mold structure (first layer) made of PDMS material and a masking film (second layer) made of silicone material having a thickness of about 100 to 200 μm were equally manufactured. A hole of the masking film (second layer) was manufactured so as to match the engraved groove position of the mold structure (first layer).

On top of the manufactured mold structure (first layer), the masking film (second layer) was attached to fit in the engraved groove position to manufacture a double-layered mold.

Step 3. Manufacture of a Microneedle With an Attached Masking Film

As a microneedle manufacturing solution, poly(lactide) was heated to a temperature over a melting point to prepare it in a melted state.

The prepared microneedle manufacturing solution was supplied and applied to the double-layered structure mold prepared in the step 2 and was cured by cooling, and then the mold structure (first layer) was removed to manufacture a microneedle in which a masking film was attached.

Step 4. Manufacture of a Coated Microneedle

The coating solution prepared in the step 1 was coated or attached to the microneedle by a spraying or dipping method and was dried, and then finally, the masking film was removed to prepare a microneedle in which coating is formed only on a fine needle part.

The invention claimed is:

1. A method for manufacturing a microneedle comprising a coating part on a needle tip, comprising
(i) preparing a microneedle mold having a double-layered structure, by attaching a second layer comprising a masking film having holes on top of a first layer comprising a mold having microneedle-shaped fine engraved patterns,
wherein there is no misalignment between the holes of the masking film and the microneedle-shaped fine engraved patterns;
(ii) injecting a needle-forming polymer composition into the mold having the double-layered structure;
(iii) curing the injected composition to form a microneedle structure;
(iv) removing the first layer to expose a needle tip of the formed structure;
(v) coating the exposed needle tip with a coating solution; and
(vi) removing the second layer,
wherein the step (i) is carried out before the step (ii); and wherein the step (v) is carried out before the step of (vi).

2. The method according to claim 1, wherein the masking film comprises one or more selected from the group consisting of silicone, polyurethane, polyethylene, polyester, polypropylene, poly vinyl chloride and polyethylene terephthalate.

3. The method according to claim 1, wherein the coating solution comprises one or more selected from the group consisting of hyaluronic acid, sodium carboxymethyl cellulose, vinyl pyrrolidone-vinyl acetate copolymer, polyvinyl alcohol, polyvinyl pyrrolidone and saccharide.

4. The method according to claim 3, wherein the coating solution further comprises one or more active ingredients selected from nucleic acids, proteins, peptides, polysaccharides, lipids, drugs and vaccines.

5. The method according to claim 1, wherein the needle-forming polymer composition comprises one or more selected from the group consisting of hyaluronic acid; biodegradable polymers including poly(lactide), poly(glycolide), poly(lactide-co-glycolide), polyanhydride, polyorthoester, polyetherester, polycaprolactone, polyesteramide, poly(butyric acid), poly(valeric acid), polyurethane and copolymers thereof; and non-biodegradable polymers including polyacrylate, ethylene-vinyl acetate polymer, acrylic substituted cellulose acetate, non-degradable polyurethane, polystyrene, polyvinyl chloride, polyvinyl fluoride, polyvinyl imidazole), chlorosulphonate polyolefins, polyethylene oxide and copolymers thereof.

6. The method according to claim 1, wherein the coating step (v) is performed by a method of dipping or spraying.

7. The method according to claim 1, further comprising adhering a support containing an adhesive to the formed microneedle structure between the steps iii) and iv).

8. The method according to claim 7, wherein the support is a skin adhesive patch.

\* \* \* \* \*